United States Patent [19]
Fox

[11] Patent Number: 6,085,746
[45] Date of Patent: Jul. 11, 2000

[54] OSCILLATING VENTILATOR APPARATUS AND METHOD

[75] Inventor: Donald M. Fox, Anaheim, Calif.

[73] Assignee: Sensormedics Corporation, Yorba Linda, Calif.

[21] Appl. No.: 09/040,014

[22] Filed: Mar. 17, 1998

[51] Int. Cl.[7] .................................................. A61M 16/00
[52] U.S. Cl. ............................. 128/204.19; 128/204.25; 128/204.21
[58] Field of Search ......................... 128/204.18, 204.19, 128/204.21, 204.25

[56] References Cited

U.S. PATENT DOCUMENTS

| | | | |
|---|---|---|---|
| 4,719,910 | 1/1988 | Jensen | 128/204.21 |
| 4,838,257 | 6/1989 | Hatch | 128/204.19 |
| 5,307,794 | 5/1994 | Rauterkus et al. | 128/204.18 |
| 5,339,807 | 8/1994 | Carter | 128/204.21 |
| 5,755,223 | 5/1998 | Schaible et al. | 128/204.21 |
| 5,771,884 | 6/1998 | Yarnall et al. | 128/204.19 |
| 5,881,722 | 3/1999 | DeVries et al. | 128/204.21 |

*Primary Examiner*—Aaron J. Lewis
*Attorney, Agent, or Firm*—Lyon & Lyon LLP

[57] ABSTRACT

An improved high frequency oscillating ventilator apparatus and method for providing an increased volume of gas flow into a patient and reducing the noise generated by the ventilator. A plurality of magnets drives a coil to produce adequate volume of flow to ventilate a larger child or an adult. Suspension elements composed of synthetic materials suspend the coil. A muffler, an air entrainment hose, and a low-voltage evacuation fan provide sound suppression.

17 Claims, 2 Drawing Sheets

OSCILLATING VENTILATOR APPARATUS AND METHOD

FIELD OF THE INVENTION

This invention generally relates to ventilation of air breathing mammals, and more particularly to an improved oscillating ventilatory apparatus.

BACKGROUND OF THE INVENTION

The invention relates generally to ventilators for supporting ventilation in air breathing mammals, both humans and animals. More particularly, the present invention relates to high frequency ventilators which operate by supplying oscillatory respiratory gases to a patient at a frequency above the normal breathing frequency of the patient.

High frequency oscillating ventilators are well known and have been previously described in, e.g., U.S. Pat. No. 4,719,910, which is incorporated herein by reference in its entirety. Unlike conventional ventilators which ventilate by positive-pressured gas flow and rely on passive recoil of the lung tissue for expiration, high frequency oscillating ventilators employ an active expiratory phase in which gas is pushed into and pulled out of a patient's lungs during alternate cycles of the oscillating diaphragm (or piston) of the ventilator. The forward motion of the diaphragm (toward the patient) creates a positive-going pressure relative to the static pressure in the patient's airway. As the diaphragm is driven rearward from its most forward position, the dynamic pressure it generates reverses from positive-going to negative-going. This bipolar dynamic pressure waveform is the principal reason for the success of the high frequency oscillatory ventilator in providing improved respiratory gas exchange.

A problem that has been encountered in the use of high frequency oscillating ventilators of the type disclosed in the aforesaid U.S. Pat. No. 4,719,910 is that the volume of air it can deliver to a patient is limited, making such ventilators suitable only for young children. Consequently, older children and adults in a critical care environment may not benefit from the advantages of this high frequency oscillating ventilator.

Another problem that has been encountered in the use of high frequency oscillating ventilators is noise. Users have complained that the high frequency oscillatory ventilator is loud when compared with other equipment in the intensive care unit. This noise comes from several sources. First, air used to cool the coil exits through holes at the rear of the driver. These holes allow a sputtering sound at the driver frequency to pass unhindered to the surrounding environment from the driver. Further, the outrush of air through these holes produces additional noise. Second, ambient air rushing to the air entrainment port of the ventilator creates a constant high frequency noise. Third, the evacuation fan within the ventilator enclosure creates a whining noise. Taken together, these three factors create a significant amount of unwanted noise. This noise can be disruptive to communications between caregivers, unsettling to young patients dependent upon the device, and annoying to other patients nearby.

Finally, cotton is currently used as the material for the coil suspension elements. Over time, cotton is susceptible to mechanical fatigue, resulting in tearing and failure.

SUMMARY OF THE INVENTION

The present invention is directed toward an improved high-frequency oscillating ventilator for ventilating larger children and adults.

In a first aspect of the invention, the preferred embodiment of the improved oscillating ventilator includes two abutting toroidal magnets bonded together with adhesive. A piston wound with conductive wiring reciprocates within the center cavity formed by the center portions of the two magnets.

In a second aspect of the invention, a fan within the improved oscillating ventilator enclosure operates at the lowest voltage at which it can still disperse leaked oxygen or other ventilatory gases that may accumulate to unsafe concentrations within the enclosure. This low voltage operation reduces fan noise, and thereby the total noise generated by the improved high-frequency oscillating ventilator.

In a third aspect of the invention, the preferred embodiment of the improved oscillating ventilator includes an air inlet located at the base of the enclosure. Placing this inlet at the base of the enclosure, away from the patient's head, reduces the noise perceived by the patient.

In a fourth aspect of the invention, the improved oscillating ventilator includes a sound muffler connected to the holes through which cooling air exits the rear of the driver. This muffler further reduces the noise generated by the improved high-frequency oscillating ventilator.

In a fifth aspect of the invention, the improved oscillating ventilator includes coil suspension elements composed of synthetic material to increase the resistance of those elements to wear.

DETAILED DESCRIPTION OF THE PREFERRED EMBODIMENTS

Figure 1:
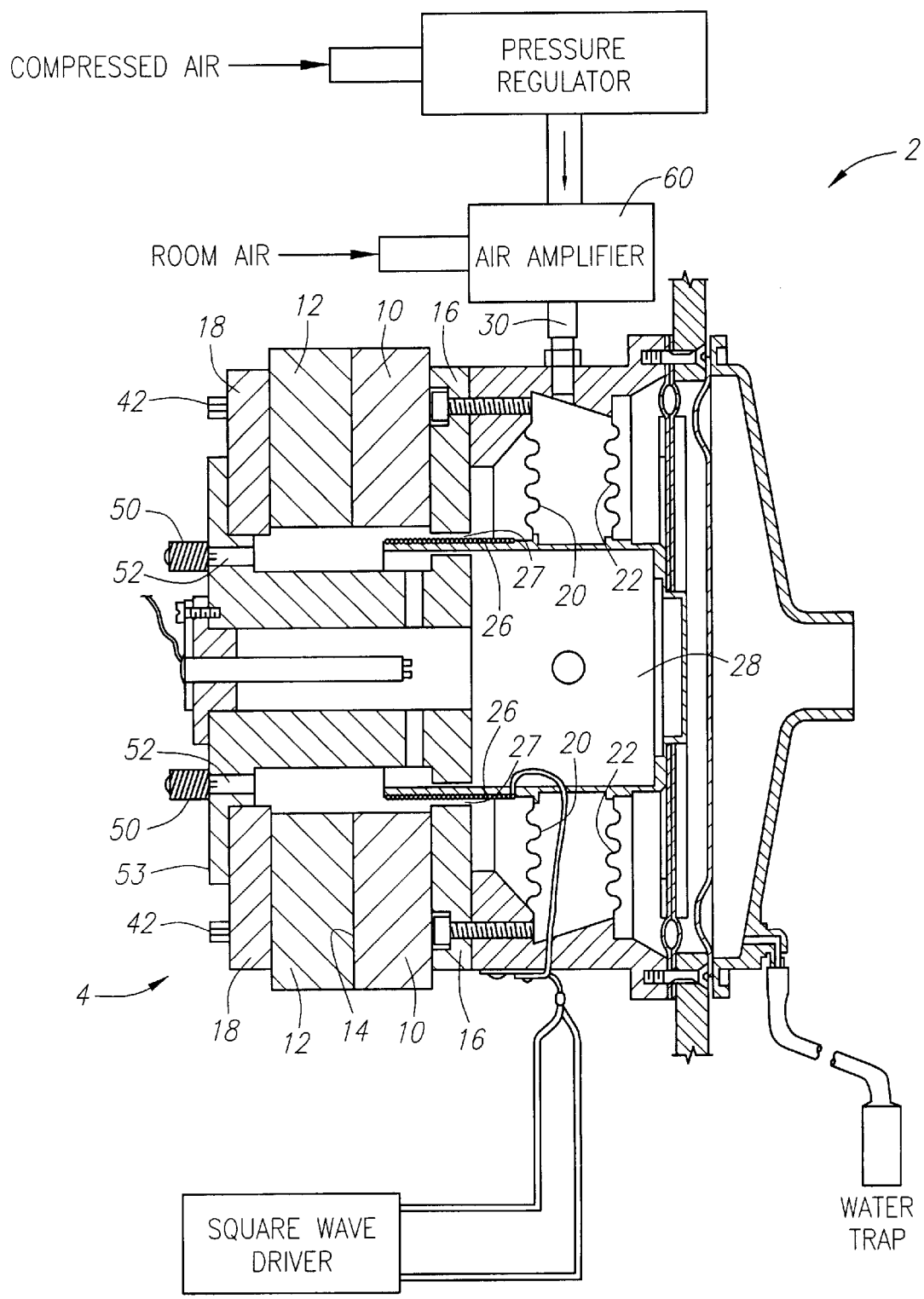
FIG. 1 is a schematic vertical partial section view illustrating an assemblage of major components for a high frequency oscillating ventilator.

Referring to FIG. 1, there are shown the elements commonly used in a high frequency oscillating ventilator apparatus of the type described in U.S. Pat. No. 4,719,910, but incorporating the current invention. The conventional portions of the apparatus will therefore be mentioned only from the standpoint of their relationship to the current invention.

Thus, FIG. 1 shows an improved high frequency oscillating ventilator 2, containing a plurality of magnets. A driver 4 is a subcomponent of the improved oscillatory ventilator apparatus, as disclosed in U.S. Pat. No. 4,719,910. Preferably, two toroidal ceramic magnets are mounted within said improved high frequency oscillating ventilator 2, a front magnet 10 and a rear magnet 12. The diameters of the holes at the center of said front magnet 10 and said rear magnet 12 are substantially the same. Said front magnet 10 and said rear magnet 12 are positioned in contact with each other, and are oriented such that the opposite poles of said front magnet 10 and said rear magnet 12 are in contact and the holes in the centers of said front magnet 10 and said rear magnet 12 are substantially aligned. Preferably, said front magnet 10 and said rear magnet 12 are mounted in a demagnetized state and then magnetized together. If said front magnet 10 and said rear magnet 12 are mounted in a magnetized state, preferably the south pole of said front magnet 10 faces and magnetically engages the north pole of said rear magnet 12. Preferably, adhesive is applied at a junction 14 between said front magnet 10 and said rear magnet 12 to ensure the proper alignment is maintained between the two magnets. However, mechanical fasteners such as bolts can be used to hold the magnets together. Said front magnet 10 and said rear magnet 12 are sandwiched between a front plate 16 and a back plate 18. A plurality of screws, bolts, or other fasteners 42 fasten said front plate 16 to said back plate 18 in order to clamp said front magnet 10 and said rear magnet 12 therebetween. Said front plate 16 and said back plate 18 possess a toroidal shape.

The center holes in the toroidal shapes of said front magnet 10, said rear magnet 12, said front plate 16, and said rear plate 18 together form a hollow cylindrical cavity. A pole piece 53, preferably constructed of steel, attaches to the rear plate and extends into that cavity as far as said front plate 16. The portion of said pole piece 53 that extends into that cavity is cylindrical, and does not touch said front magnet 10 or said rear magnet 12. The pole piece 53 does not touch said front plate 16. Instead, an air gap 27 exists between said pole piece 53 and said front plate 16. Said air gap 27 extends around the entire inner circumference of the toroidal front plate 16. Magnetic flux travels between said pole piece 53 and said front plate 16 through said air gap 27. The pole piece provides a low impedance path for magnetic flux.

A coilform 28 possesses the form of a hollow thin-walled cylinder closed in front and open at the rear. A coil 26 is wound around a portion of the rear of said coilform 28. The rear portion of said coilform 28 is positioned within the space between said pole piece 53 and said front magnet 10, said rear magnet 12, said front piece 16, and said rear piece 18. Said coilform 28 is positioned such that a portion of said coil 26 is located within said air gap 27. Said coil 26 is overhung. That is, said coil 26 extends along a greater length of said coilform 28 than the length of said air gap 27, which is equivalent to the thickness of said front plate 16.

In the preferred embodiment, said coilform 28 is suspended by a first coil suspension spider 20 and a second coil suspension spider 22 which attach to the inner walls of said driver 4. Said first coil suspension spider 20 and said second coil suspension spider 22 are composed of synthetic material, to increase resistance to mechanical fatigue and tearing. Preferably, said first coil suspension spider 20 and said second coil suspension spider 22 are composed of NOMEX (TM).

When current is applied to said coil 26, interaction between said coil 26 and the magnetic flux traveling through said air gap 27 causes said coilform 28 to move axially. When said current is reversed, said coilform 28 moves axially in the opposite direction. Consequently, said coilform 28 reciprocates axially.

Gases pass through radially spaced passages 52 in said pole piece 53 while said improved high frequency oscillating ventilator 2 operates. Preferably, said driver 4 possesses twelve radially spaced passages 52, located in said pole piece 53 and positioned at a equal linear distance from the radial centerline of said driver 4 and at an equal angular distance from each other. A muffler 50 is attached to said driver 4 at the exit of each radially spaced passage 52. Said mufflers 50 reduce the noise created by gas flow out of the improved high frequency oscillating ventilator 2. Preferably, each muffler 50 consists of a tightly-wound spring capped with a head, through which air escapes from between the coils. However, any muffling device which reduces noise and creates low enough backpressure to prevent interference with the operation of said driver 4 may be used.

Figure 2:
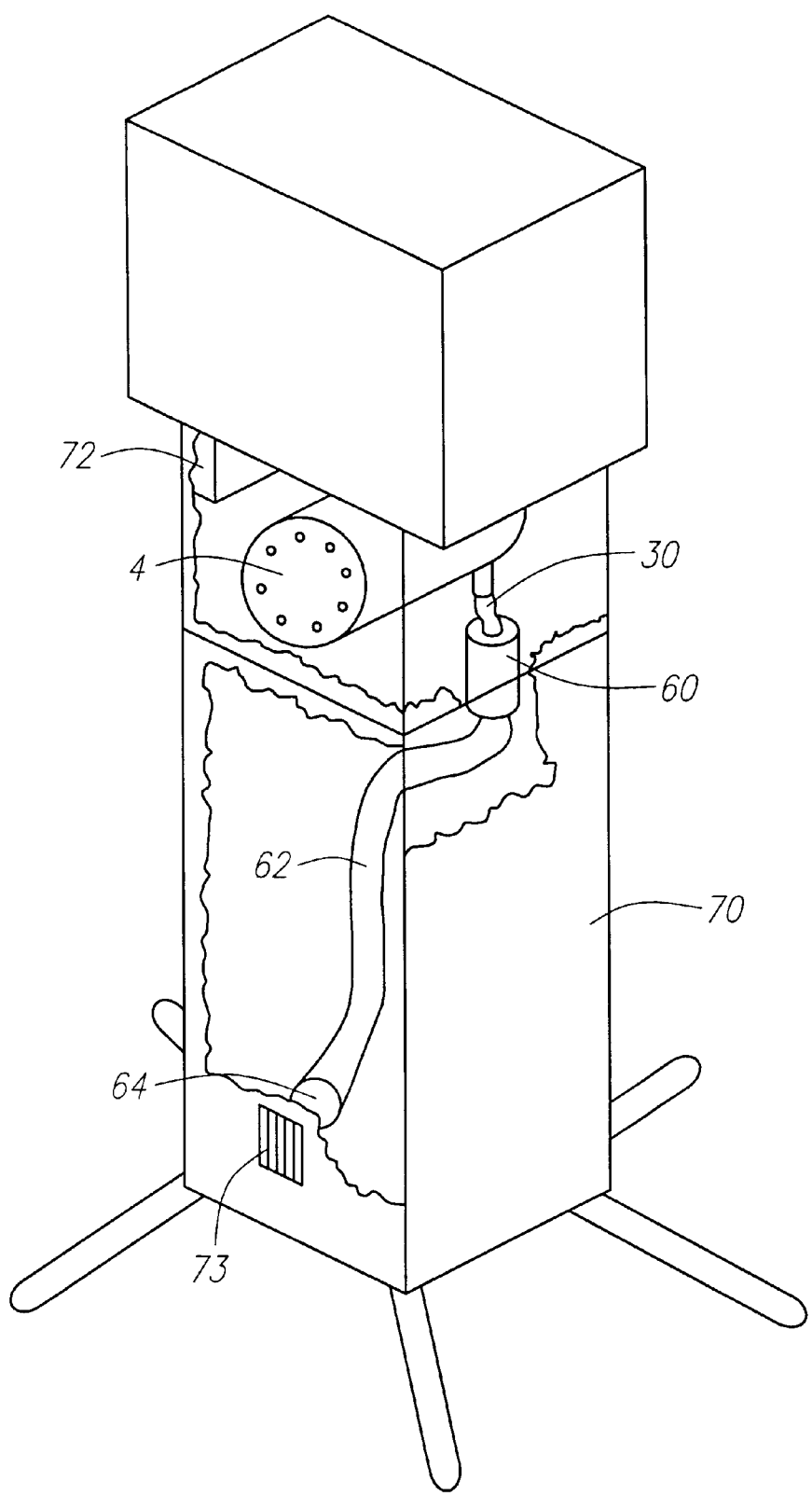
FIG. 2 is a perspective view of the high frequency oscillatory ventilator constructed according to the present invention.

Referring now to FIG. 2, said improved oscillating ventilator 2 provides a greater volume of gas to a patient. In addition, said improved oscillatory ventilator 2 generates a greater amount of heat. Consequently, a greater volume of gas must be furnished to said improved high frequency oscillating ventilator 2 both for introduction into the patient and for cooling said driver 4.

Said driver 4 requires up to 40 LPM of airflow for cooling. In order to generate a flow rate that large, the improved high frequency oscillating ventilator advantageously includes an air amplifier 60. Said air amplifier 60 operates on the venturi principle. Pressure at the throat of the venturi is less than the ambient atmospheric pressure outside the venturi. Therefore, as gases enter said air amplifier 60 from a source such as a compressed gas tank or a blower, the pressure of those gases at the venturi in said air amplifier 60 is lower than ambient atmospheric pressure. By placing at least one air entrainment port at the venturi, the pressure difference between the venturi and the outside atmosphere forces ambient air into said air amplifier 60 through the air entrainment port, resulting in a greater volume of gas passing through said air amplifier 60 into said improved high frequency oscillating ventilator 2. An entrainment hose 62 is attached to the air entrainment port. Said entrainment hose 62 is routed down the inside of an enclosure 70 which contains the majority of components of said improved high frequency oscillating ventilator 2, so that the inlet 64 of said entrainment hose 62 is preferably located at the base of said enclosure 70. However, said inlet 64 could be located at any point in the enclosure. Noise is generated as air enters said inlet 64. The placement of the inlet 64 at the base of said enclosure 70 minimized the noise from the inlet 64 that reaches the patient. Further, advantageous placement of the inlet 64 at the base of said enclosure 70 allows for the intake of cooler air located at approximately floor level, resulting in more efficient cooling of the driver 4. Said inlet 64 is preferably located near a filtered opening 73. Said filtered opening 73 filters incoming air to remove macroscopic contaminants, and preferably bacterial, fungal, and other microscopic contaminants as well. Said air amplifier 60 draws ambient air through said entrainment hose 62. Subsequently, air passes from said air amplifier 60 to said driver 4 through a pipe 30.

When oxygen is administered to a patient by said improved high frequency oscillating ventilator 2, a possibility exists that the concentration of oxygen within said enclosure 70 may rise to levels that present a risk of combustion. An enclosure fan 72 is disposed within said enclosure 70 to disperse oxygen or other gases that may collect within said enclosure 70. Said enclosure fan 72 creates a flow of ambient air through said enclosure 70, and draws that ambient air and any gases leaking from said improved high frequency oscillating ventilator 2 out of said enclosure 70. The buildup of oxygen poses the greatest risk, due to the danger of combustion. Therefore, said enclosure fan 72 is sized to meet safety requirements for the prevention of oxygen buildup. An oxygen concentration of 24% or greater is generally considered unsafe. Consequently, a flow rate must be generated within said enclosure 70 that is adequate to prevent a concentration of oxygen of 24% from accumulating within. To minimize noise, said enclosure fan 72 should operate at the lowest voltage at which safety requirements are met. In the preferred embodiment, a 10VDC fan operates at a flow rate of 26 SCFM, which is adequate to disperse a pure oxygen worst-case leak of 2.25 SCFM.

A preferred improved high frequency oscillating ventilator apparatus and method and many of its attendant advantages have thus been disclosed. It will be apparent, however, that various changes may be made in the form, construction, and arrangement of the parts without departing from the spirit and scope of the invention, the form hereinbefore described being merely a preferred or exemplary embodiment thereof. Therefore, the invention is not to be restricted or limited except in accordance with the following claims.

What is claimed is:

1. An improved high frequency oscillating ventilator, comprising:
    a source of one or more gases;
    a housing including a plurality of magnets and having a diaphragmatically sealed piston mounted therein, said piston having a first side and a second side;
    a first hose conducting the flow of a gas or gases from said gas source to the space within said housing on the first side of said piston;
    a coilform mounted to the first side of said piston within said housing;
    a coil wound around at least part of said coilform;
    a second hose conducting the flow of a gas or gases from said gas source to the space within said housing on the second side of said piston;
    a tube connecting the space within said housing on the second side of said piston and the airway of a patient; and
    a controller for delivering current to said coil operable to reverse the polarity of the current in said coil, thereby causing said coilform to move back and forth within said housing relative to said magnets to move said piston to alternately produce a positive and negative pressure wave in the flow of gas in said tube.

2. The improved high frequency oscillating ventilator of claim 1, wherein said plurality of magnets comprises two magnets.

3. The improved high frequency oscillating ventilator of claim 1, wherein said magnets are placed adjacent to one another such that a pole of one magnet abuts the opposite pole of an adjacent magnet.

4. The improved high frequency oscillating ventilator of claim 1, wherein said magnets are bonded together by an adhesive.

5. The improved high frequency oscillating ventilator of claim 1, further comprising an air amplifier and an entrainment hose, wherein said entrainment hose is positioned such that it its inlet is located in the bottom portion of the improved high frequency oscillating ventilator.

6. The improved high frequency oscillating ventilator of claim 1, further comprising at least one coil suspension spider composed of synthetic material.

7. The improved high frequency oscillating ventilator of claim 1, wherein said coil is overhung.

8. An improved high frequency oscillating ventilator, comprising:
    a source of one or more gases;
    a housing including a plurality of magnets and having a diaphragmatically sealed piston mounted therein, said piston having a first side and a second side;
    one or more mufflers attached to said housing at one or more points where gas exits said housing into the atmosphere;
    a first hose conducting the flow of a gas or gases from said gas source to the space within said housing on the first side of said piston;
    a coilform mounted to the first side of said piston within said housing;
    a coil wound around at least part of said coilform;
    a second hose conducting the flow of a gas or gases from said gas source to the space within said housing on the second side of said piston;
    a tube connecting the space within said housing on the second side of said piston and the airway of a patient; and
    a controller for delivering current to said coil operable to reverse the polarity of the current in said coil, thereby causing said coilform to move back and forth within said housing relative to said magnets to move said piston to alternately produce a positive and negative pressure wave in the flow of gas in said tube.

9. An improved high frequency oscillating ventilator, comprising:
    a source of one or more gases;
    a housing including a plurality of magnets and having a diaphragmatically sealed piston mounted therein, said piston having a first side and a second side;
    a first hose conducting the flow of a gas or gases from said gas source to the space within said housing on the first side of said piston;
    a coilform mounted to the first side of said piston within said housing;
    a coil wound around at least part of said coilform;
    a second hose conducting the flow of a gas or gases from said gas source to the space within said housing on the second side of said piston;
    a tube connecting the space within said housing on the second side of said piston and the airway of a patient;
    a controller for delivering current to said coil operable to reverse the polarity of the current in said coil, thereby causing said coilform to move back and forth within said housing relative to said magnets to move said piston to alternately produce a positive and negative pressure wave in the flow of gas in said tube;
    an enclosure containing the housing; and
    an evacuation fan operating at or below 10 volts DC to provide at least 26 SCFM of evacuation flow from the enclosure.

10. A driver for a high frequency oscillating ventilator comprising:
    a housing including a plurality of magnets, having a diaphragmatically sealed piston mounted therein, said piston having a first side and a second side;
    a first connector connecting the space within said housing on the first side of said piston to a first gas conducting line;
    a coilform mounted to the first side of said piston;
    a coil wound around at least part of said coilform;
    at least one passage in said housing for directing the flow of gas delivered to the space within said housing on the first side of said piston by said first gas conducting line around said coil and through said housing to the atmosphere, thereby cooling said coil;
    a second connector connecting the space within said housing on the second side of said piston to a second gas conducting line; and
    a controller for delivering current to said coil operable to reverse the polarity of the current in said coil, thereby causing said coil to move back and forth within said housing relative to said magnets to alternately produce a positive and negative pressure wave in a flow of gas from said second gas conducting line.

11. The driver of claim 10, wherein said plurality of magnets comprises two magnets.

12. The improved high frequency oscillating ventilator of claim 10, wherein said coil is overhung.

13. A method for ventilating a mammalian patient at high frequency, comprising the steps of:

introducing a flow of ventilatory gas into a housing, said housing having a diaphragmatically sealed piston mounted therein, said piston having a first side and a second side;

generating a magnetic field with a plurality of toroidal magnets located within said housing;

delivering current to a coil wrapped around at least part of a coilform mounted within a cylindrical space formed within said plurality of magnets, said coilform being mounted to the first side of the piston, said coilform being located inside said housing;

causing said coilform to reciprocate within said cylindrical space and said magnetic field within said plurality of magnets by inducing changes in the polarity of said current in said coil;

producing a positive and negative pressure wave in said flow of ventilatory gas by directing said flow of ventilatory gas to the second side of said piston; and directing said positive and negative pressure wave into the airway of a patient.

14. The method of claim 13, wherein said magnetic field is generated by two magnets.

15. The method of claim 13, further comprising the step of collecting ventilatory gas through an entrainment hose such that the inlet of said entrainment hose is located in the bottom portion of said improved high frequency oscillatory ventilator.

16. A method for ventilating a mammalian patient at high frequency, comprising the steps of:

introducing a flow of ventilatory gas into a housing, said housing having a diaphragmatically sealed piston mounted therein, said piston having a first side and a second side;

generating a magnetic field with a plurality of toroidal magnets located within said housing;

delivering current to a coil wrapped around at least part of a coilform mounted within a cylindrical space formed within said plurality of magnets, said coilform being mounted to the first side of the piston, said coilform being located inside said housing;

causing said coilform to reciprocate within said cylindrical space and said magnetic field within said plurality of magnets by inducing changes in the polarity of said current in said coil;

producing a positive and negative pressure wave in said flow of ventilatory gas by directing said flow of ventilatory gas to the second side of said piston;

directing said positive and negative pressure wave into the airway of a patient;

expelling waste gas from the housing, and muffling the flow of expelled waste gases from said housing.

17. A method for ventilating a mammalian patient at high frequency, comprising the steps of:

introducing a flow of ventilatory gas into a housing, said housing having a diaphragmatically sealed piston mounted therein, said piston having a first side and a second side;

generating a magnetic field with a plurality of toroidal magnets located within said housing;

delivering current to a coil wrapped around at least part of a coilform mounted within a cylindrical space formed within said plurality of magnets, said coilform being mounted to the first side of the piston, said coilform being located inside said housing;

causing said coilform to reciprocate within said cylindrical space and said magnetic field within said plurality of magnets by inducing changes in the polarity of said current in said coil;

producing a positive and negative pressure wave in said flow of ventilatory gas by directing said flow of ventilatory gas to the second side of said piston;

directing said positive and negative pressure wave into the airway of a patient;

expelling waste gas from the housing, and evacuating gas from within an enclosure of the improved high-frequency oscillating ventilator with a fan operating at or below 10 volts DC and providing at least 26 SCFM of evacuation flow.

\* \* \* \* \*